United States Patent [19]

Lavoie et al.

[11] Patent Number: 5,811,686

[45] Date of Patent: Sep. 22, 1998

[54] TEST FIXTURE FOR DETERMINATION OF ENERGY ABSORBING CAPABILITIES OF COMPOSITE MATERIALS

[75] Inventors: J. Andre Lavoie, Blacksburg; Karen E. Jackson, Poquoson, both of Va.; John Morton, Oxford, England

[73] Assignee: The United States of America as represented by the Administrator of the National Aeronautics and Space Administration, Washington, D.C.

[21] Appl. No.: 881,626

[22] Filed: Jun. 24, 1997

Related U.S. Application Data

[63] Continuation of Ser. No. 306,556, Sep. 13, 1994, abandoned.
[51] Int. Cl.$^6$ ................................. G01N 3/08; G01N 3/02
[52] U.S. Cl. .................................................. 73/821; 73/856
[58] Field of Search ................................ 73/11.01, 12.01, 73/12.06, 12.09, 12.13, 821, 855, 856

[56] References Cited

U.S. PATENT DOCUMENTS

| | | | |
|---|---|---|---|
| 3,443,423 | 5/1969 | Ma | 73/821 |
| 3,545,251 | 12/1970 | Munn | 73/12.09 |
| 3,693,421 | 9/1972 | Karper et al. | 73/12.01 |
| 5,297,441 | 3/1994 | Smith et al. | 73/860 |
| 5,305,634 | 4/1994 | Suga et al. | 73/856 |

OTHER PUBLICATIONS

K. Jackson et al., "Scaling of energy composite plates", AHS 48th Annual Forum, Washington, DC, Jun. 3–5, 1992, pp. 1431–1440.

ASTM Standards D 695–91, "Standard test method for compressive properties of rigid plastics", pp. 82–87.

ASTM Standards D 3410M–95, "Standard test method of compressive prp[erties of polymer matrix composite materials with unsupported gage section shear loading", pp. 129–144.

*Primary Examiner*—Richard Chilcot
*Assistant Examiner*—Max H. Noori
*Attorney, Agent, or Firm*—Robin W. Edwards

[57] ABSTRACT

The present invention provides a fixture for supporting an elongated specimen for crush testing. The fixture comprises a base plate, four guiding rods, a sliding plate, four support rods and two collars. The guiding rods connect to the base plate and extend in a direction substantially perpendicular to the base plate. The sliding plate has linear bearings which encircle the guiding rods and enable translation of the sliding plate along the axis of each guiding rod. The four supporting rods mount to the base plate and also extend in a direction substantially perpendicular to the base plate. Each support rod has a keyway for a wedge which contacts the elongated specimen and holds the specimen in place during crushing. Each collar lies above the sliding plate and holds a pair of support rods on their ends opposite the ends connected to the base plate. A spherical bearing sits on top of the sliding plate and transfers an applied load to the sliding plate, which moves downward and crushes the elongated specimen.

12 Claims, 6 Drawing Sheets

TEST FIXTURE FOR DETERMINATION OF ENERGY ABSORBING CAPABILITIES OF COMPOSITE MATERIALS

This is a continuation of application Ser. No. 08/306,556 filed on Sep. 13, 1994, which is now abandoned.

ORIGIN OF THE INVENTION

The invention described herein was jointly made by a graduate student, a NASA employee and a grantee employee during the performance of work under NASA Grant NAG-1-343. In accordance with 35 U.S.C. 202, the grantee elected not to retain title.

BACKGROUND OF THE INVENTION

1. Field of the Invention

The invention relates generally to crush testing, and more particularly to a fixture for supporting an elongated specimen during crush testing.

2. Related Art of the Invention

One of the goals of manufacturers of rotorcraft and light, fixed wing aircraft is to design crashworthy structures, i.e., structures which protect their occupants against injury and which also minimize damage to equipment in the event of a crash. Designing for crashworthiness requires a total systems approach which means each part of the structure should dissipate a portion of the energy from a crash. Accordingly, manufacturers of rotorcraft and light fixed wing aircraft need test methods for studying the energy-absorbing capability of materials used to construct rotorcraft and aircraft. Typically, these materials are lightweight, high-strength composite materials.

Examples of related methods for determining the energy-absorbing potential of composite materials includes the tube crushing method. The tube crushing method involves the fabrication of a cylindrical tube which has a trigger mechanism machined on one end to serve as a site for crushing initiation. A compressive load is applied until the desired stroke is obtained. The energy absorbed in the tube crushing process is the area under the load deflection curve. Shortcomings of the tube crushing method include: (1) tubes are expensive to fabricate and difficult to manufacture in a reliable manner especially when using a hand-layup technique; (2) the energy absorption values measured from tube crushing tests are idealized because of the self-stabilizing nature of the tube structure, and (3) tubes are not practical structural elements for realistic designs of aircraft subfloors, making the data obtained from tube tests inapplicable to structural designs which incorporate plates.

Another example of a test fixture for composite plates comprises four vertical rods fixed at one end in a steel base plate. The four rods provide lateral support for an elongate specimen and also serve as a guide for motion of a sliding plate. A compressive load is applied to the sliding plate, which in turn applies a crushing load to the specimen. Shortcomings of this method include global buckling, binding of the support rods with the sliding plate, and inaccurate test data because the frictional loads between the support rods and the sliding plate are a major fraction of the measured load.

Other related art includes U.S. Pat. No. 5,297,441 by Smith et al. Smith et al. disclose an apparatus for stabilizing an elongated specimen in a compression testing machine. The apparatus supports the test piece along its lengthwise edge or edges to prevent unwanted Euler buckling, yet the device allows sublaminate buckling to occur. The apparatus includes grip plates which are mounted to the test machine and which engage a portion of the elongated specimen while the remainder of the specimen is supported along its lengthwise edges by its stabilizing plates. Shortcomings of this art include: (1) limited range of deformation, which is insufficient for obtaining energy absorption data, (2) capability of testing only one size of an elongated specimen, and (3) an elaborate design which does not allow for crushed debris to escape.

SUMMARY OF THE INVENTION

Accordingly, an object of the present invention is to perform crush tests on flat plate or elongated specimens. Another object is to allow crush testing of specimens of different sizes.

Another object is to promote crushing rather than global buckling of compressively-loaded plates.

Another object of the invention is to examine the effect of alternate trigger mechanism geometries, used to initiate crushing, on crushing characteristics.

Yet another object is to enable crush testing with dynamic loads.

The present invention obtains the foregoing and additional objects by providing a fixture for supporting an elongated specimen for crush testing. The fixture comprises a base plate, four guiding rods, a sliding plate, four support rods, a spherical bearing and two collars. The guiding rods connect to the base plate and extend in a direction substantially perpendicular to the base plate. The sliding plate has four linear bearings which encircle the guiding rods and enable translation of the sliding plate along the axis of the guiding rods. The four supporting rods mount to the base plate and also extend in a direction substantially perpendicular to the base plate. Each support rod has a keyway which receives a wedge. Each wedge contacts the elongated specimen and holds the specimen in place. The wedge is adjustable to accommodate specimens of different thicknesses. Each collar lies above the sliding plate and holds a pair of support rods on their ends opposite the ends connected to the base plate. A spherical bearing sits in a centering dimple on top of the sliding plate and transfers an applied load to the sliding plate while eliminating the possibility of applied bending moments. The sliding plate then moves downward and crushes the elongated specimen.

BRIEF DESCRIPTION OF THE DRAWINGS

For a more complete understanding of the present invention and for further objects and advantages thereof, reference is now made to the following description taken in conjunction with the accompanying drawings in which.

DETAILED DESCRIPTION OF THE INVENTION

Figure 1:
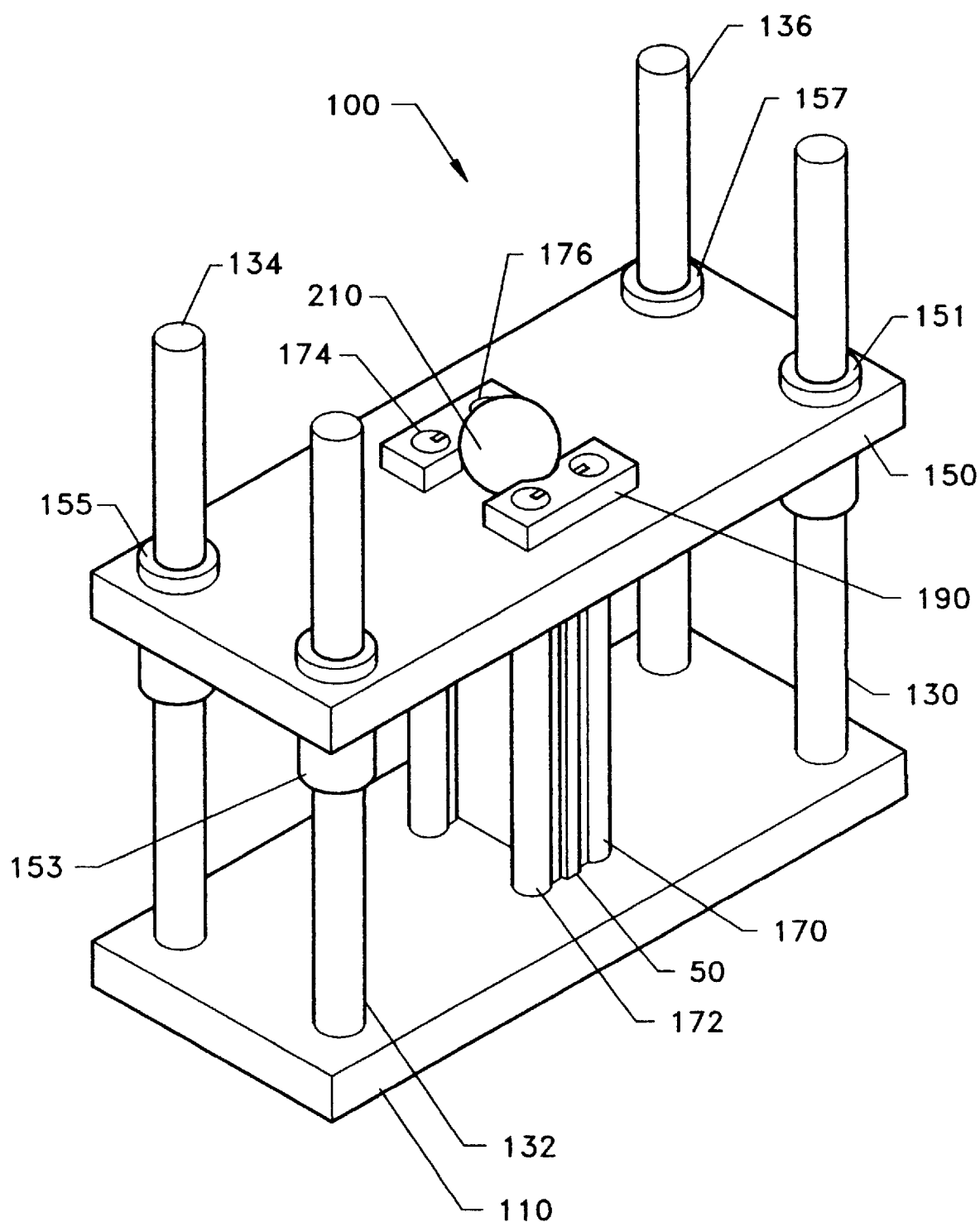
FIG. 1 is a perspective view of a test fixture for supporting an elongated specimen during crush testing in accordance with the present invention.
Figure 2:
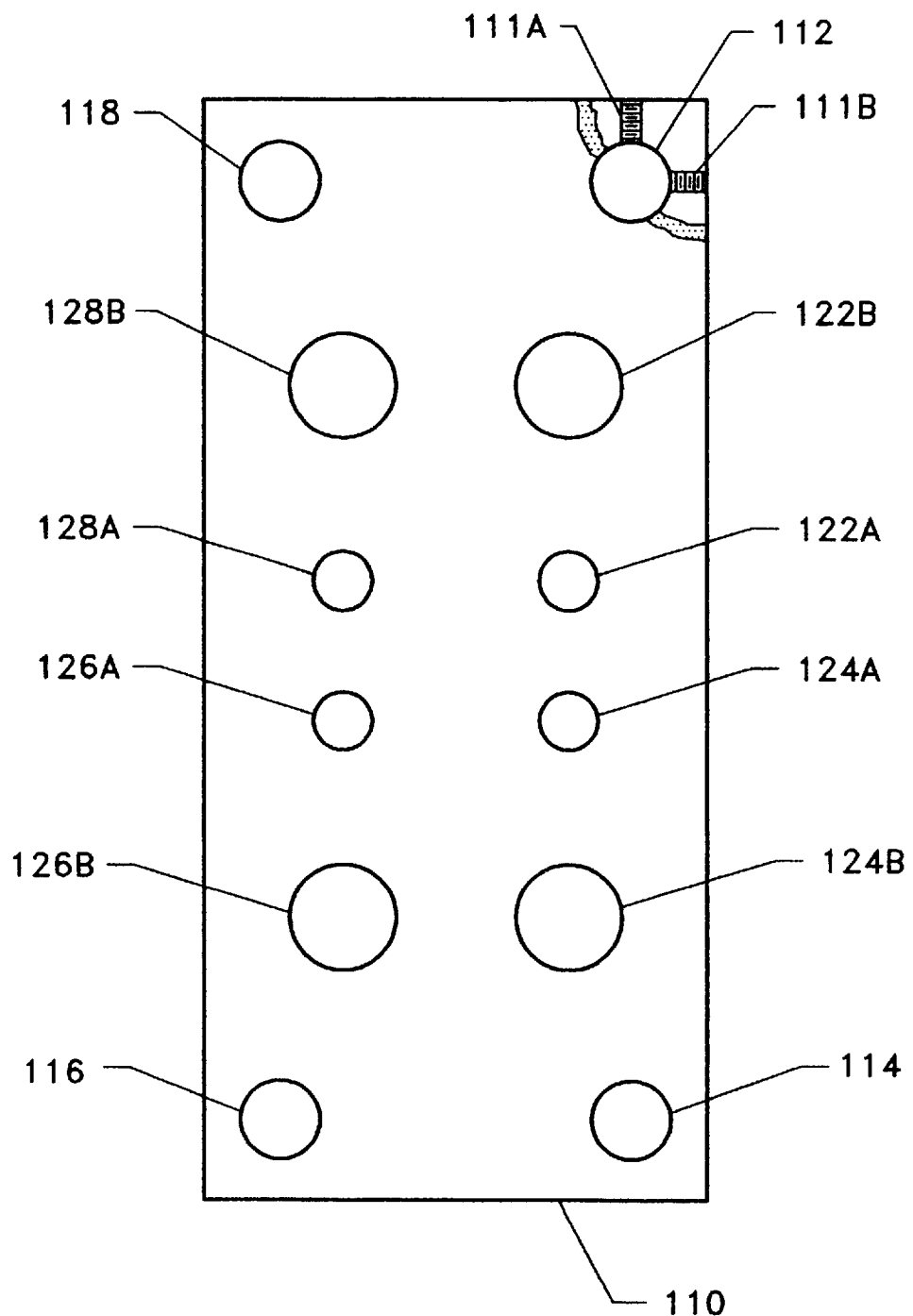
FIG. 2 is a top view of a base plate in accordance with the present invention.
Figure 3:
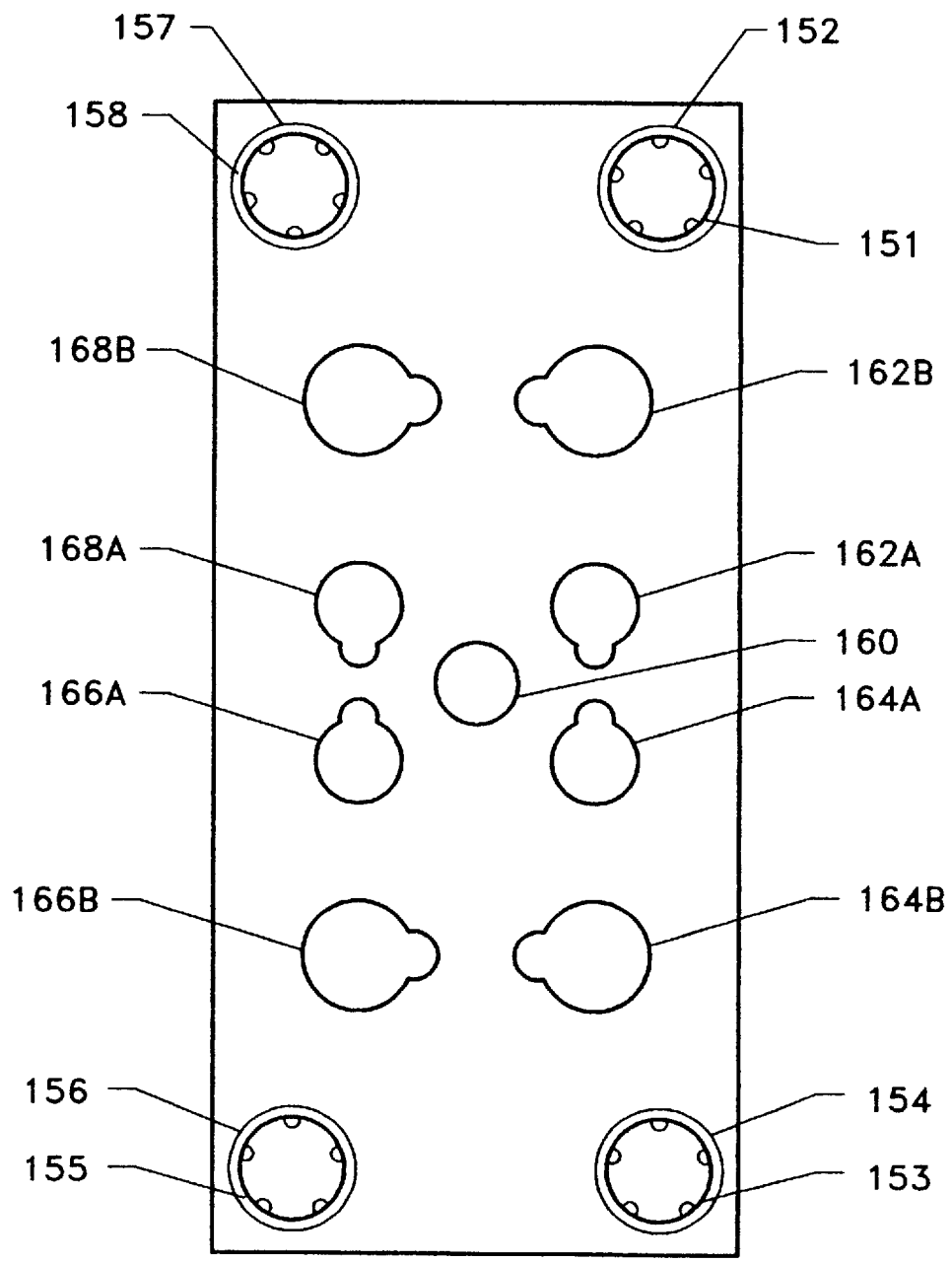
FIG. 3 is a top view of a sliding plate in accordance with the present invention.

Referring now to FIGS. 1–3, a fixture for supporting an elongated specimen for crush testing, shown generally as reference numeral 100, comprises a base plate 110, four guiding rods 130, 132, 134, and 136, a sliding plate 150, four supporting rods 170, 172, 174 and 176, two supporting rod collars 190 and 196, and a spherical bearing 210. The base plate 110 has two sets of four circular holes machined to receive and support the four guiding rods and the four support rods. The circular holes 112, 114, 116 and 118 for the guiding rods are each located near a different corner of the plate 110. The guiding rods 130, 132, 134 and 136 fixedly attach to the plate within the holes 112, 114, 116, and 118, respectively, located in the corners of the base plate 110 and extend in a direction substantially perpendicular to the plate.

The supporting rods 170, 172, 174 and 176 fixedly attach to the plate 110 within the holes 122A, 124A, 126A and 128A, respectively, located within the middle of the base plate 110. Alternatively, the supporting rods 170, 172, 174 and 176 may fixedly attach to the plate 110 within the holes 122B, 124B, 126B, and 128B, respectively. The position of the holes for receiving the supporting rods depends on the size of the elongated specimen 50. Varying the dimensions of the specimen enables one to study the effects of specimen size on energy-absorbing capabilities. The holes for the supporting rods 122A–128A and 122B–128B shown in FIG. 2 are for a 2×3 specimen and a 4×6 specimen, respectively.

The base plate 110 may have an additional pair of bores 111A and 111B tapped at 90° angles from each hole 112–118 for receiving the guiding rods. The bores 111A and 111B each receive a setting screw for securing the guide rod into its upright position. Each guide rod accordingly has two small indentations to receive the two setting screws. The guiding rods, the supporting rods, and the base plate may be made of steel.

The sliding plate 150 is preferably rectangular and similar in size to the base plate 110. The sliding plate 150 has two sets of pass-through holes. One set of four holes 152, 154, 156 and 158 is for receiving the four guiding rods, while the second set of four holes 162A, 164A, 166A, 168A, or 162B, 164B, 166B and 168B is for receiving the support rods. As with the base plate, the set of holes 152–158 for the guiding rods are located near a different corner of the sliding plate 150. The position of the set of holes for the supporting rods depends on the size of the elongated specimen. The two sets of holes for the supporting rods, 162A–168A and 162B–168B shown in FIG. 3 are for a 2×3 specimen and a 4×6 specimen, respectively. The holes 162A–168A or 162B–168B in the sliding plate for the support rods are not completely circular but instead have a semi-circular notch in opposite facing directions along the inner portion of the plate 150 near where the elongated specimen 50 is located. The sliding plate 150 also has a dimple 160 for centering the load transferred to the sliding plate. The sliding plate may be made of steel.

Referring to FIGS. 1 and 3, the sliding plate 150 includes four linear bearings 151, 153, 155 and 157 which fit within the holes 152–158, respectively. Each linear bearing 151–157 is a ball bushing which encircles a different guiding rod 130–136, respectively, and enables nearly frictionless travel of the sliding plate along the guiding rods.

Figure 4:
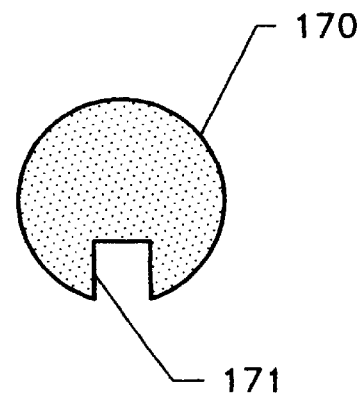
FIGS. 4 and 5 are overhead views of supporting rods with wedges in accordance with the present invention.
Figure 5:
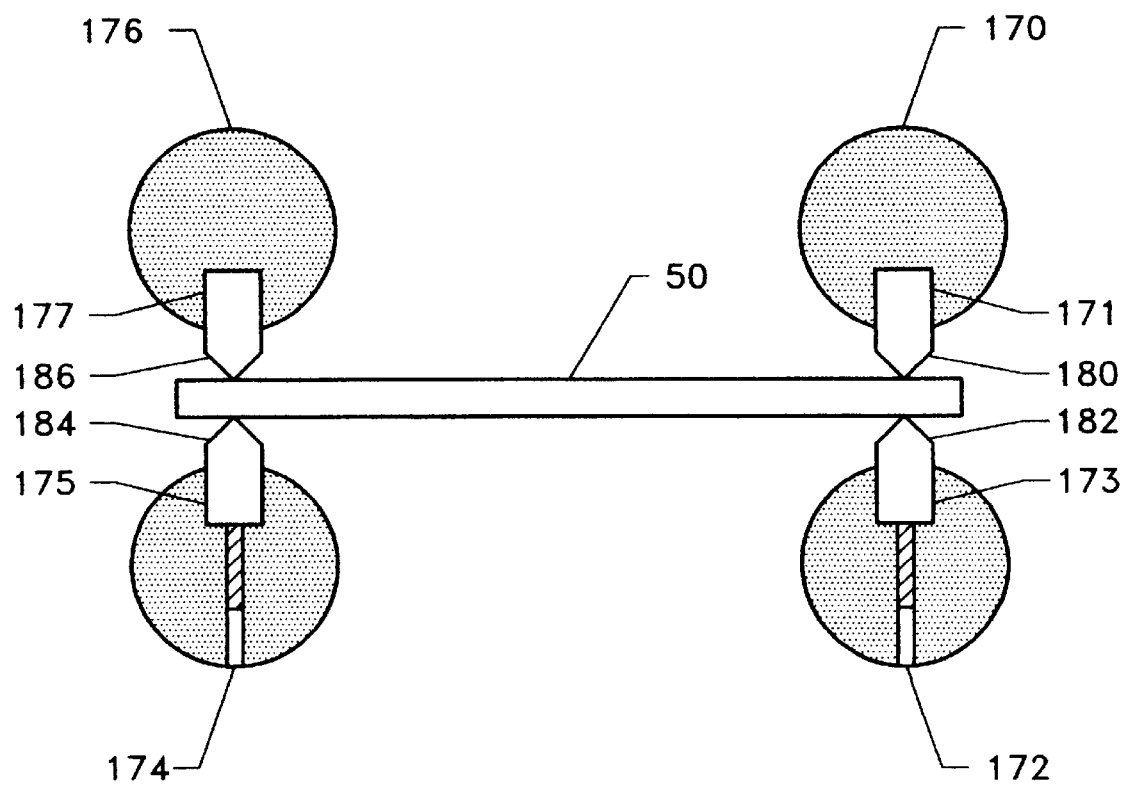

Referring now to FIGS. 4 and 5, each supporting rod 170, 172, 174 and 176 has a keyway 171, 173, 175 and 177, respectively, notched along the axis of the rod. Four wedges 180, 182, 184 and 186 each having a knife-edge fit within a different keyway of each support rod. The wedges 180–186 extend from the support rod and contact the elongated specimen 50 to stabilize the specimen during crushing. The wedges are adjustable to accommodate specimens of different thicknesses.

Figure 6A:
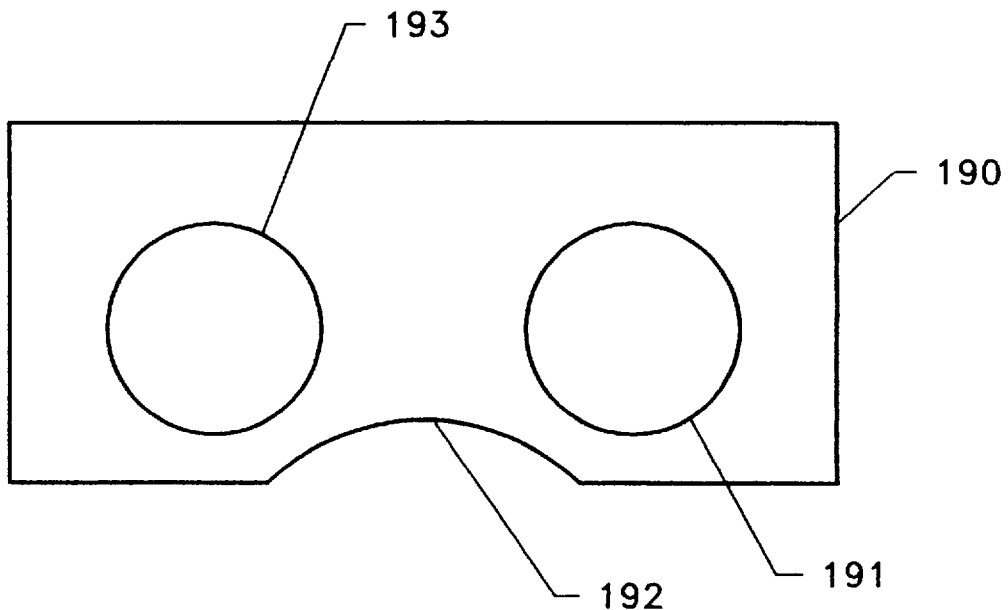
FIGS. 6A and 6B are top views of two collars in accordance with the present invention.
Figure 6B:
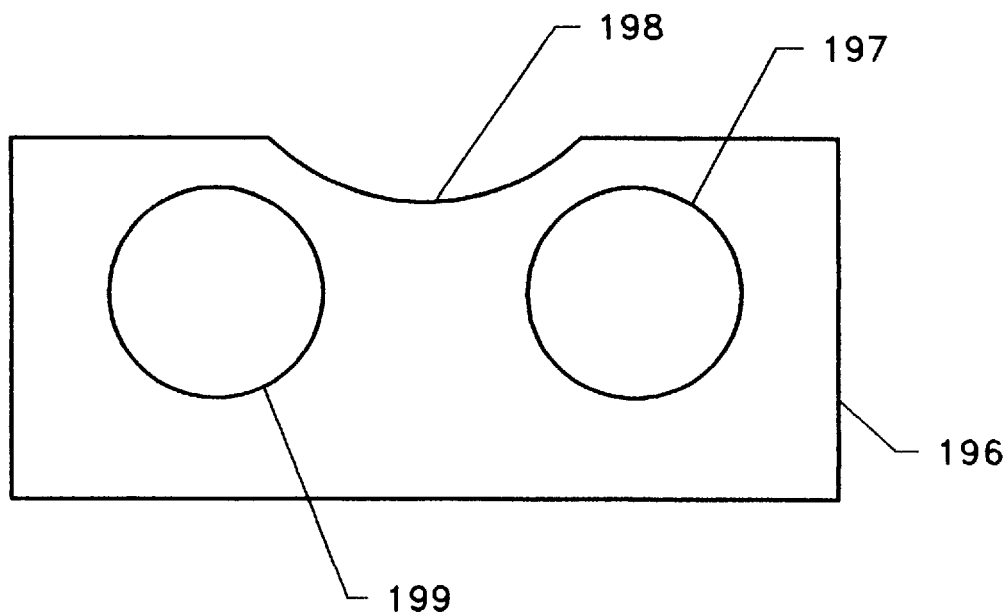

FIGS. 6A and 6B illustrate the collars 190 and 196 each having a pair of holes 191, 193 and 197, 199, respectively, for receiving the other end of the supporting rods. The collars 190 and 196 also each have a semi-circular notch 192 and 198, respectively, for receiving the spherical bearing. The collars may be made of steel.

Referring now to FIGS. 1, 3, 6A and 6B, the collars 190 and 196 each lie above the sliding plate 150 and attach to a different pair of supporting rods. The direction in which each collar attaches to the pair of supporting rods is substantially perpendicular to the direction in which the elongated specimen extends. The collars 190 and 196 ensure that the elongated specimen is supported along its entire length by controlling any spreading of the supporting rods which may occur during crushing. The collars also ensure the supporting rods do not contact the sliding plate.

The spherical bearing 210, which may be made of steel, sits on top of the sliding plate in the dimple 160 and between the two semi-circular notches 192 and 198 of the collars. The spherical bearing receives an applied load and eliminates any bending moments by providing a point load to the sliding plate.

The novel features of this invention include an outer set of guiding rods whose only function is to guide the sliding plate and linear bearings which provide nearly frictionless travel along the guiding rods. Other novel features include supporting rods which have no contact with the sliding plate, wedges which fit into the keyways of the supporting rods, and a spherical bearing to receive the applied load.

The advantages of the present invention include the capability of testing different sizes of specimens with the same test fixture, no interference of the fixture with the load measurements, no interference of the support rods with the free travel of the sliding plate, adjustable wedges which accommodate elongated specimens having slightly different thicknesses, reduction in the likelihood of global buckling, and lower costs of fabrication of materials to perform crush testing. Another advantage includes the capability of this fixture to be used for dynamic loading.

OPERATION OF THE INVENTION

Figure 7:
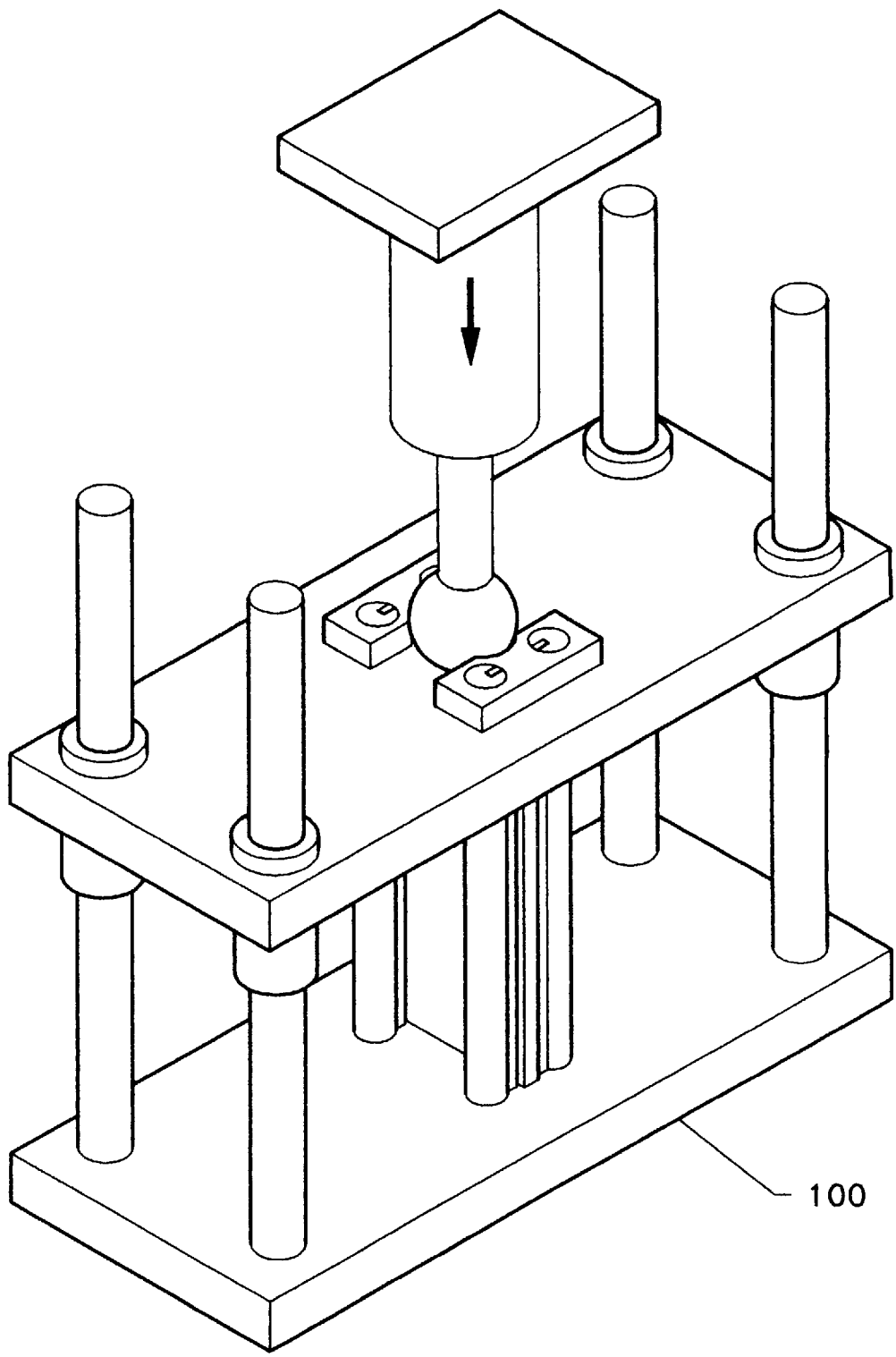
FIG. 7 is a perspective view of the test fixture placed under a loading machine just before crush testing in accordance with the present invention.

As illustrated in FIG. 7, the procedure for conducting a crush test with the fixture 100 includes the following steps: 1) center the elongated specimen between the support rods; 2) obtain line support along the elongated specimen by using set screws to adjust the wedges; 3) engage the sliding plate with the guiding rods; 4) install the collars over the other end of the supporting rods; 5) place the spherical bearing on the centering dimple located on the sliding plate; 6) position a loading rod of a loading machine over the spherical bearing; 7) set the testing machine to the proper cross-head displacement rate and begin loading; and, 8) stop the test when the desired displacement or stroke is achieved.

Although the invention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

What is claimed as new and desired to be secured by Letters Patent of the United States is:

1. A fixture for supporting an elongated specimen for crush testing, comprising:

a base plate;

four guiding rods, fixedly attached to said base plate, said guiding rods extending in a direction substantially perpendicular to said base plate;

a sliding plate, loosely connected to said guiding rods, for crushing the elongated specimen in a direction substantially perpendicular to said base plate;

four supporting rods, connected on one end to said baseplate, for supporting the elongated specimen, said supporting rods extending in a direction substantially perpendicular to said base plate, said supporting rods located to provide lateral restraint along the longitudinal edges of the elongated specimen during crushing by said base plate and said sliding plate; and two collars, each attached at the other ends of a different pair of said supporting rods, for securing said supporting rods during crush testing and for preventing said supporting rods from contacting said sliding plate.

2. A fixture for supporting an elongated specimen for crush testing as recited in claim 1 wherein said base plate has bores for receiving said guiding rods and said supporting rods.

3. A fixture for supporting an elongated specimen for crush testing as recited in claim 1 wherein said base plate, said sliding plate, and said collars are made of steel.

4. A fixture for supporting an elongated specimen for crush testing as recited in claim 1 wherein said guiding rods and said supporting rods are made of steel.

5. A fixture for supporting an elongated specimen for crush testing as recited in claim 1 wherein said sliding plate further comprises four linear bearings, each linear bearing encircling a different guiding rod.

6. A fixture for supporting an elongated specimen for crush testing comprising:

a base plate:

four guiding rods, fixedly attached to said base plate, said guiding rods extending in a direction substantially perpendicular to said base plate;

a sliding plate, loosely connected to said guiding rods, for crushing the elongated specimen in a direction substantially perpendicular to said base plate;

four supporting rods, connected on one end to said baseplate, for supporting the elongated specimen, wherein each said supporting rod has a keyway extending along its axis and positioned near the elongated specimen; and two collars, each attached at the other ends of a different pair of said supporting rods, for securing said supporting rods during crush testing and preventing said supporting rods from contacting said sliding plate.

7. A fixture for supporting an elongated specimen for crush testing as recited in claim 6 wherein each said supporting rod includes a wedge fitted within each keyway for contacting and holding the elongated specimen.

8. A fixture for supporting an elongated specimen for crush testing, comprising:

a base plate;

four guiding rods, fixedly attached to said base plate, said guiding rods extending in a direction substantially perpendicular to said base plate;

a sliding plate, loosely connected to said guiding rods, for crushing the elongated specimen in a direction substantially perpendicular to said base plate;

four supporting rods, connected on one end to said base plate, for supporting the elongated specimen;

two collars, each attached at the other ends of a different pair of said supporting rods, for securing said supporting rods during crush testing and preventing said supporting rods from contacting said sliding plate; and a spherical bearing positioned on top of said sliding plate and between the two collars for transferring a point load to said sliding plate.

9. A fixture for supporting an elongated specimen for crush testing as recited in claim 8 wherein said sliding plate further comprises a circular recess located on the upper surface of said sliding plate, said recess being shaped for receiving said spherical bearing.

10. A fixture for supporting an elongated specimen for crush testing as recited in claim 8 wherein said spherical bearing is made of steel.

11. A fixture for supporting an elongated specimen for crush testing, comprising:

a base plate;

a plurality of guiding rods, fixedly attached to said base plate, said plurality of guiding rods extending in a direction substantially perpendicular to said base plate;

means, loosely connected to said plurality of guiding rods, for crushing the elongated specimen in a direction substantially perpendicular to said base plate;

means, connected on one end to said base plate, for supporting the elongated specimen, said means located to provide lateral restraint along the longitudinal edges of the elongated specimen during crush testing by said base plate and said sliding plate; and two collars, each attached at the other end of said means for supporting, for stabilizing said means for supporting during crush testing and preventing said means for supporting from contacting said means for crushing.

12. A fixture for supporting an elongated specimen for crush testing, comprising:

a base plate;

a plurality of guiding rods, fixedly attached to said base plate, said plurality of guiding rods extending in a direction substantially perpendicular to said base plate;

means, loosely connected to said plurality of guiding rods, for crushing the elongated specimen in a direction substantially perpendicular to said base plate; means, connected on one end to said base plate, for supporting the elongated specimen;

two collars, each attached at the other end of said means for supporting, for stabilizing said means for supporting during crush testing and for preventing said means for supporting from contacting said means for crushing; and a spherical bearing positioned on top of said means for crushing and between the two collars for transferring a point load to said crushing means.

* * * * *